United States Patent
Guglielmi et al.

[11] Patent Number: 6,066,133
[45] Date of Patent: *May 23, 2000

[54] ENDOVASCULAR ELECTROLYTICALLY DETACHABLE WIRE AND TIP FOR THE FORMATION OF THROMBUS IN ARTERIES, VEINS, ANEURYSMS, VASCULAR MALFORMATIONS AND ARTERIOVENOUS FISTULAS

[75] Inventors: Guido Guglielmi, Santa Monica; Ivan Sepetka, Redwood City, both of Calif.

[73] Assignee: The Regents of the University of California, Oakland, Calif.

[*] Notice: This patent is subject to a terminal disclaimer.

[21] Appl. No.: 08/944,826

[22] Filed: Oct. 6, 1997

Related U.S. Application Data

[63] Continuation of application No. 08/801,795, Feb. 14, 1997, Pat. No. 5,855,578, which is a continuation of application No. 08/485,821, Jun. 6, 1995, abandoned, which is a division of application No. 08/311,508, Sep. 23, 1994, Pat. No. 5,540,680, which is a continuation of application No. 07/840,211, Feb. 24, 1992, Pat. No. 5,354,295, which is a continuation-in-part of application No. 07/492,717, Mar. 13, 1990, Pat. No. 5,122,136.

[51] Int. Cl.$^7$ .................................................. A61B 18/08
[52] U.S. Cl. .............................. 606/32; 606/41; 606/108; 606/191
[58] Field of Search .................................. 606/32, 41, 49, 606/28, 108, 191; 600/529, 585; 604/104; 607/122; 623/1, 12

[56] References Cited

U.S. PATENT DOCUMENTS

| | | |
|---|---|---|
| 4,512,338 | 4/1985 | Balko et al. . |
| 4,735,201 | 4/1988 | O'Reilly . |
| 4,739,768 | 4/1988 | Engelson . |
| 4,748,986 | 6/1988 | Morrison et al. . |
| 4,820,298 | 4/1989 | Leveen et al. . |
| 4,884,579 | 12/1989 | Engelson . |
| 4,994,069 | 2/1991 | Ritchart et al. . |
| 5,108,407 | 4/1992 | Geremia et al. . |
| 5,122,136 | 6/1992 | Guglielmi et al. .................. 606/32 |

FOREIGN PATENT DOCUMENTS

| | | |
|---|---|---|
| WO 91/13592 | 9/1991 | WIPO . |
| WO 92/01425 | 2/1992 | WIPO . |
| WO 93/11825 | 6/1996 | WIPO . |

OTHER PUBLICATIONS

Target Therapeutics, "History of the Guglielmi Detachable Coil," History of the GDC, pp. 1–6 Oct. 1995.

Guglielmi et al., "Intravascular Electrothrombosis in Experimentally Induced Vascular Malformation," Assoziazone Italiani di Neuroradiologia, Sep. 29–30, 1983, pp. 139–146.

Sadato et al., "Immediately Detachable Coil for Aneurysms Treatment," ANJR 16: 1459–1462 Aug. 1995.

(List continued on next page.)

*Primary Examiner*—Lee Cohen
*Attorney, Agent, or Firm*—Daniel L. Dawes

[57] ABSTRACT

An artery, vein, aneurysm, vascular malformation or arterial fistula is occluded through endovascular occlusion by the endovascular insertion of a platinum wire and/or tip into the vascular cavity. The vascular cavity is packed with the tip to obstruct blood flow or access of blood in the cavity such that the blood clots in the cavity and an occlusion if formed. The tip may be elongate and flexible so that it packs the cavity by being folded upon itself a multiple number of times, or may pack the cavity by virtue of a filamentary or fuzzy structure of the tip. The tip is then separated from the wire mechanically or by electrolytic separation of the tip from the wire. The wire and the microcatheter are thereafter removed leaving the tip embedded in the thrombus formed within the vascular cavity. Movement of wire in the microcatheter is more easily tracked by providing a radioopaque proximal marker on the microcatheter and a corresponding indicator marker on the wire. Electrothrombosis is facilitate by placing the ground electrode on the distal end of the microcatheter and flowing current between the microcatheter electrode and the tip.

47 Claims, 6 Drawing Sheets

OTHER PUBLICATIONS

Mullan, "Eperiences with Surgical Thrombosis of Intracranial Berry Aneurysms and Carotid Cavernous Fistulas", J. Neurosurg., vol. 41, Dec. 1974, pp. 657–670.

Hosobuchi, "Electrothrombosis Carotid–Cavernous Fistula", J. Neurosurg., vol. 42, Jan. 1975, pp. 76–85.

Araki et al., "Electrically Induced Thrombosis for the Treatment of Intracranial Aneurysms and Angiomas", Excerpta Medica International Congress Series, Amsterdam 1965, vol. 110, pp. 651–654.

Sawyer et al., "Bio–Electric Phenomena as an Etiological Factor in Intravascular Thrombosis", Am., J. Physiol., vol. 175, pp. 103–107 (1953).

J. Piton et al., "Selective Vascular Thrombosis Induced by a Direct Electrical Current; Animal Experiments", J. Neuroradiology, vol. 5, pp. 139–152 (1978).

Anderson et al, "Transcathter Intravascular Coil Occulsion of Experimental Arteriovenous Fistulas", AM. J. Roentgenol. vol. 129, pp. 795–798, Nov. 1977.

Zuniga et al, "A New Device for Safe Delivery of Stainless Steel Coils" Radiology vol. 136, pp. 230–231, Jul. 1980.

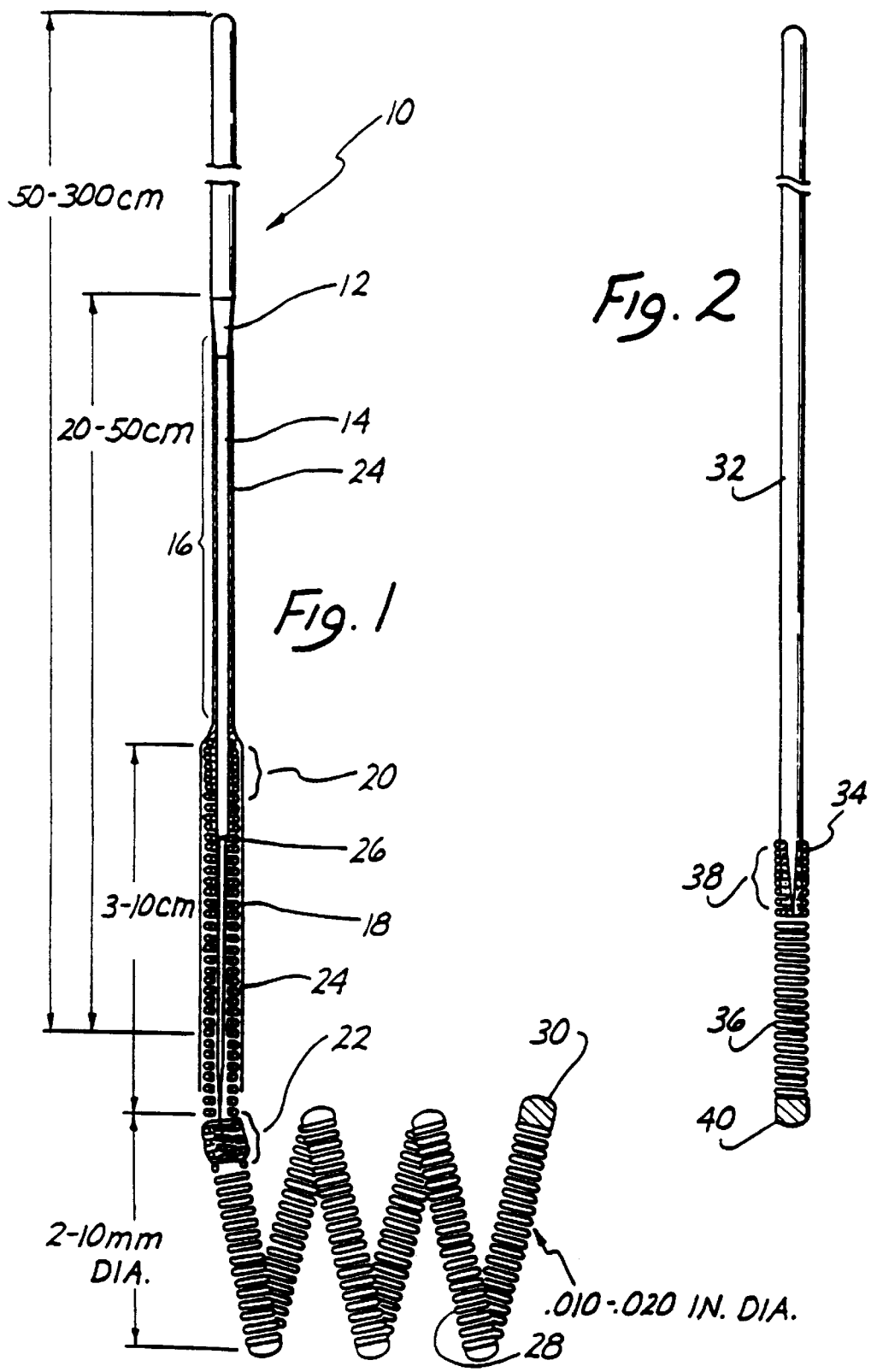

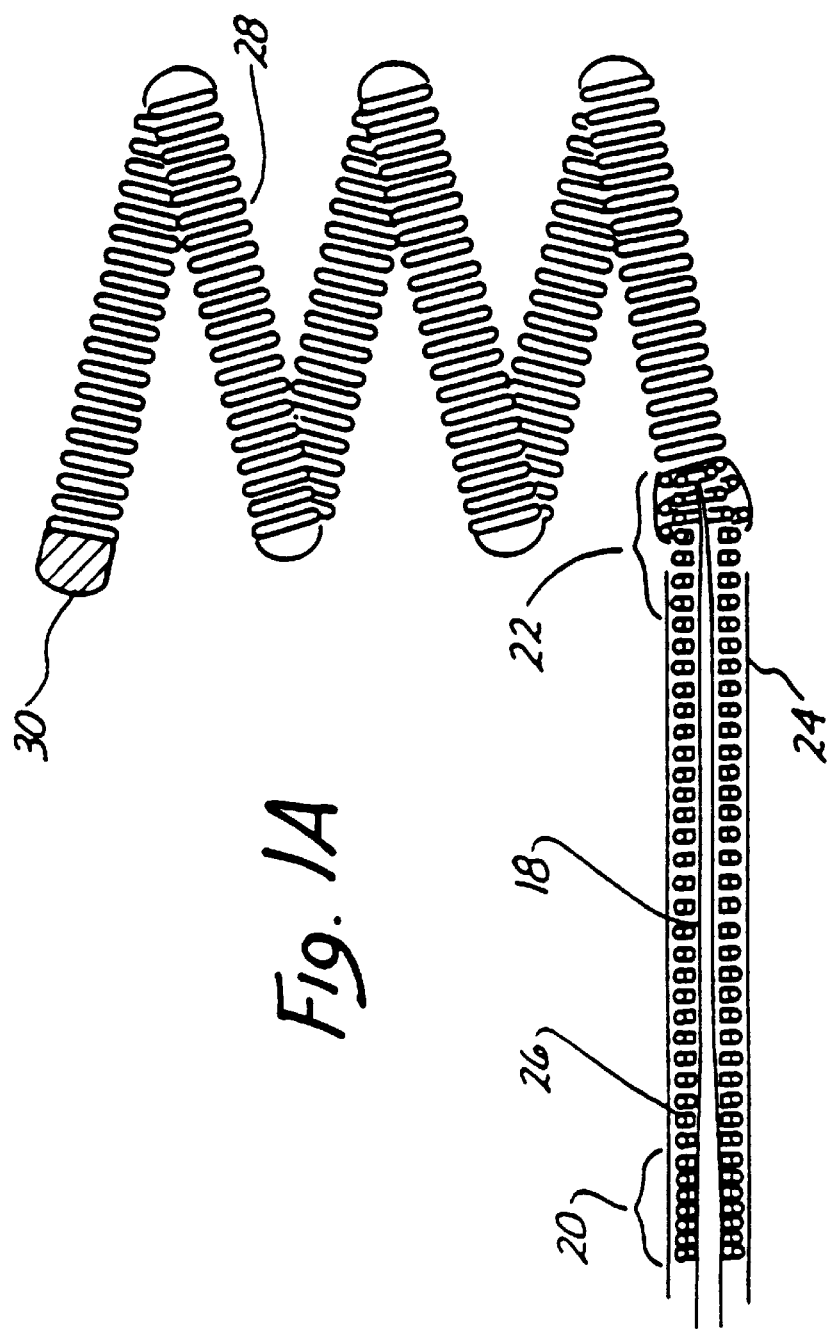
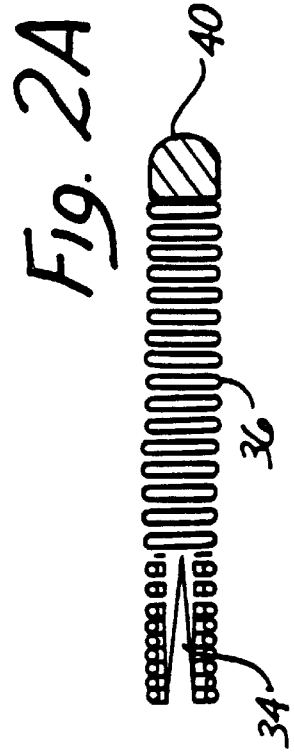

ENDOVASCULAR ELECTROLYTICALLY DETACHABLE WIRE AND TIP FOR THE FORMATION OF THROMBUS IN ARTERIES, VEINS, ANEURYSMS, VASCULAR MALFORMATIONS AND ARTERIOVENOUS FISTULAS This application is a continuation of application Ser. No. 08/801,795 filed Feb. 14, 1997, issued as U.S. Pat. No. 5,855,578, which in turn was a continuation of application Ser. No. 08/485,821, filed Jun. 6, 1995, now abandoned, and which in its turn was a continuation-in-part application of application Ser. No. 07/492,717, filed Mar. 13, 1990, issued as U.S. Pat. No. 5,122,136.

BACKGROUND OF THE INVENTION

1. Field of the Invention

The invention relates to a method and apparatus for endovascular electrothrombic formation of thrombi in arteries, veins, aneurysms, vascular malformations and arteriovenous fistulas.

2. Description of the Prior Art

Approximately 25,000 intracranial aneurysms rupture every year in North America. The primary purpose of treatment for ruptured intracranial aneurysm is to prevent rebleeding. At the present time, three general methods of treatment exist, namely an extravascular, endovascular and extra-endovascular approach.

The extravascular approach is comprised of surgery or microsurgery of the aneurysm or treatment site for the purpose of preserving the parent artery. This treatment is common with intracranial berry aneurysms. The methodology comprises the step of clipping the neck of the aneurysm, performing a suture-ligation of the neck, or wrapping the entire aneurysm. Each of these surgical procedures is performed by intrusive invasion into the body and performed from outside the aneurysm or target site. General anesthesia, craniotomy, brain retraction and arachnoid dissection around the neck of the aneurysm and placement of a clip are typically required in these surgical procedures. Surgical treatment of vascular intracranial aneurysm can expect a mortality rate of 4–8% with a morbidity rate of 18–20%. Because of the mortality and morbidity rate expected, the surgical procedure is often delayed while waiting for the best surgical time with the result that an additional percentage of patients will die from the underlying disease or defect prior to surgery. For this reason the prior art has sought alternative means of treatment.

In the endovascular approach, the interior of the aneurysm is entered through the use of a microcatheter. Recently developed microcatheters, such as those shown by Engelson, "Catheter Guidewire", U.S. Pat. No. 4,884,579 and as described in Engelson, "Catheter for Guidewire Tracking", U.S. Pat. No. 4,739,768 (1988), allow navigation into the cerebral arteries and entry into a cranial aneurysm.

In such procedures a balloon is typically attached to the end of the microcatheter and it is possible to introduce the balloon into the aneurysm, inflate it, and detach it, leaving it to occlude the sac and neck with preservation of the parent artery. While endovascular balloon embolization of berry aneurysms is an attractive method in situations where an extravascular surgical approach is difficult, inflation of a balloon into the aneurysm carries some risk of aneurysm rupture due to possible over-distention of portions of the sac and due to the traction produced while detaching the balloon.

While remedial procedures exist for treating a ruptured aneurysm during classical extravascular surgery, no satisfactory methodology exists if the aneurysm breaks during an endovascular balloon embolization.

Furthermore, an ideal embolizing agent should adapt itself to the irregular shape of the internal walls of the aneurysm. On the contrary, in a balloon embolization the aneurysmal wall must conform to the shape of the balloon. This may not lead to a satisfactory result and further increases the risk of rupture.

Still further, balloon embolization is not always possible. If the diameter of the deflated balloon is too great to enter the intracerebral arteries, especially in the cases where there is a vasospasm, complications with ruptured intracranial aneurysms may occur. The procedure then must be deferred until the spasm is resolved and this then incurs a risk of rebleeding.

In the extra-intravascular approach, an aneurysm is surgically exposed or stereotaxically reached with a probe. The wall of the aneurysm is then perforated from the outside and various techniques are used to occlude the interior in order to prevent it from rebleeding. These prior art techniques include electrothrombosis, isobutyl-cyanoacrylate embolization, hog-hair embolization and ferromagnetic thrombosis.

In the use of electrothrombosis for extra-intravascular treatment the tip of a positively charged electrode is inserted surgically into the interior of the aneurysm. An application of the positive charge attracts white blood cells, red blood cells, platelets and fibrinogen which are typically negatively charged at the normal pH of the blood. The thrombic mass is then formed in the aneurysm about the tip. Thereafter, the tip is removed. See Mullan, "Experiences with Surgical Thrombosis of Intracranial Berry Aneurysms and Carotid Cavernous Fistulas", J. Neurosurg., Vol. 41, December 1974; Hosobuchi, "Electrothrombosis Carotid-Cavernous Fistula", J. Neurosurg., Vol. 42, January 1975; Araki et al., "Electrically Induced Thrombosis for the Treatment of Intracranial Aneurysms and Angiomas", Excerpta Medica International Congress Series, Amsterdam 1965, Vol. 110, 651–654; Sawyer et al., "Bio-Electric Phenomena as an Etiological Factor in Intravascular Thrombosis", Am. J. Physiol., Vol. 175, 103–107 (1953); J. Piton et al., "Selective Vascular Thrombosis Induced by a Direct Electrical Current; Animal Experiments", J. Neuroradiology, Vol. 5, pages 139–152 (1978). However, each of these techniques involves some type of intrusive procedure to approach the aneurysm from the exterior of the body.

The prior art has also devised the use of a liquid adhesive, isobutylcyanoacrylate (IBCA) which polymerizes rapidly on contact with blood to form a firm mass. The liquid adhesive is injected into the aneurysm by puncturing the sac with a small needle. In order to avoid spillage into the parent artery during IBCA injection, blood flow through the parent artery must be momentarily reduced or interrupted. Alternatively, an inflated balloon may be placed in the artery at the level of the neck of the aneurysm for injection. In addition to the risks caused by temporary blockage of the parent artery, the risks of seepage of such a polymerizing adhesive into the parent artery exists, if it is not completely blocked with consequent occlusion of the artery.

Still further, the prior art has utilized an air gun to inject hog hair through the aneurysm wall to induce internal thrombosis. The success of this procedure involves exposing the aneurysm sufficiently to allow air gun injection and has not been convincingly shown as successful for thrombic formations.

Ferromagnetic thrombosis in the prior art in extra-intravascular treatments comprises the stereotactic placement of a magnetic probe against the sac of the aneurysm followed by injection into the aneurysm by an injecting needle of iron microspheres. Aggregation of the microspheres through the extravascular magnet is followed by interneuysmatic thrombus. This treatment has not been entirely successful because of the risk of fragmentation of the metallic thrombus when the extravascular magnet is removed. Suspension of the iron powder in methyl methymethacrylate has been used to prevent fragmentation. The treatment has not been favored, because of the need to puncture the aneurysm, the risk of occlusion of the parent artery, the use of unusual and expensive equipment, the need for a craniectomy and general anesthesia, and the necessity to penetrate cerebral tissue to reach the aneurysm.

Endovascular coagulation of blood is also well known in the art and a device using laser optically generated heat is shown by O'Reilly, "*Optical Fiber with Attachable Metallic Tip for Intravascular Laser Coagulation of Arteries, Veins, Aneurysms, Vascular Malformation and Arteriovenous Fistulas*", U.S. Pat. No. 4,735,201 (1988). See also, O'Reilly et al., "*Laser Induced Thermal Occlusion of Berry Aneurysms: Initial Experimental Results*", Radiology, Vol. 171, No. 2, pages 471–74 (1989). O'Reilly places a tip into an aneurysm by means of an endovascular microcatheter. The tip is adhesively bonded to a optic fiber disposed through the microcatheter. Optical energy is transmitted along the optic fiber from a remote laser at the proximal end of the microcatheter. The optical energy heats the tip to cauterize the tissue surrounding the neck of the aneurysm or other vascular opening to be occluded. The catheter is provided with a balloon located on or adjacent to its distal end to cut off blood flow to the site to be cauterized and occluded. Normally, the blood flow would carry away the heat at the catheter tip, thereby preventing cauterization. The heat in the tip also serves to melt the adhesive used to secure the tip to the distal end of the optical fiber. If all goes well, the tip can be separated from the optical fiber and left in place in the neck of the aneurysm, provided that the cauterization is complete at the same time as the hot melt adhesive melts.

A thrombus is not formed from the heated tip. Instead, blood tissue surrounding the tip is coagulated. Coagulation is a denaturation of protein to form a connective-like tissue similar to that which occurs when the albumen of an egg is heated and coagulates from a clear running liquid to an opaque white solid. The tissue characteristics and composition of the coagulated tissue is therefore substantially distinct from the thrombosis which is formed by the thrombotic aggregation of white and red blood cells, platelets and fibrinogen. The coagulative tissue is substantially softer than a thrombic mass and can therefore more easily be dislodged.

O'Reilly's device depends at least in part upon the successful cauterization timed to occur no later than the detachment of the heat tip from the optic fiber. The heated tip must also be proportionally sized to the neck of the aneurysm in order to effectively coagulate the tissue surrounding it to form a blockage at the neck. It is believed that the tissue in the interior of the aneurysm remains substantially uncoagulated. In addition, the hot melt adhesive attaching the tip to the optic fiber melts and is dispersed into the adjacent blood tissue where it resolidifies to form free particles within the intracranial blood stream with much the same disadvantages which result from fragmentation of a ferromagnetic electrothrombosis.

Therefore, what is needed is an apparatus and methodology which avoids each of the shortcomings and limitations of the prior art discussed above.

BRIEF SUMMARY OF THE INVENTION

The invention is a method for forming an occlusion within a vascular cavity having blood disposed therein comprising the steps of endovascularly disposing a wire and/or tip near an endovascular opening into the vascular cavity. The wire may include a distinguishable structure at its distal end, which is termed a tip, in which case the remaining portion of the wire may be termed a guidewire. The term "wire" should be understood to collectively include both guidewires and tips and simply wires without distinct tip structures. However, the tip may also simply be the extension of the wire itself without substantial distinction in its nature. A distal tip of the wire is disposed into the vascular cavity to pack the cavity to mechanically form the occlusion within the vascular cavity about the distal tip. The distal tip is detached from the guidewire (or wire) to leave the distal tip within the vascular cavity. As a result, the vascular cavity is occluded by the distal tip, and by any thrombus formed by use of the tip.

In one embodiment, the step of detaching the distal tip from the guidewire (or wire) comprises the step of mechanically detaching the distal tip from the guidewire (or wire).

In another embodiment, the guidewire and tip (or wire) are used within a microcatheter and in the step of detaching the distal tip from the guidewire (or wire), the guidewire and tip (or wire) are longitudinally displaced within the microcatheter. The microcatheter has radio-opaque proximal and tip markers. The guidewire and tip (or wire) have collectively a single radio-opaque marker. The displacement of the guidewire and tip (or wire) moves the single radio-opaque marker to the proximity of the proximal marker on the microcatheter. At this point the tip will be fully deployed in the vascular cavity and tip separation may proceed. It is not necessary then in this embodiment to be able to see actual deployment of the tip before separation. The tip marker allows and enhances direct observation of the correct placement of the catheter tip into the opening of the vascular cavity.

In one embodiment the step of disposing the tip (or wire) into the vascular cavity to pack the cavity comprises the step of disposing a tip (or wire) having a plurality of filaments extending therefrom to pack the cavity.

In another embodiment the step of disposing the tip (or wire) into the vascular cavity to pack the cavity comprises the step of disposing a long flexible tip (or wire) folded upon itself a multiple number of times to pack the cavity.

The invention can also be characterized as a method for forming an occlusion within a vascular cavity having blood disposed therein comprising the steps of endovascularly disposing a wire within a microcatheter near an endovascular opening into the vascular cavity. The microcatheter has a distal tip electrode. The distal tip of the wire is disposed into the vascular cavity to pack the cavity to form the occlusion within the vascular cavity about the distal tip of the wire by applying a current between the distal tip electrode and the distal end of the wire packed into the cavity. The distal tip of the wire is detached from the wire to leave the distal tip of the wire within the vascular cavity. As a result, the vascular cavity is occluded by the distal tip, and by any thrombus formed by use of the tip.

The invention is also a wire for use in formation of an occlusion within a vascular cavity used in combination with a microcatheter comprising a core wire, and a detachable elongate tip portion extending the core wire for a predetermined lineal extent. The tip portion is adapted to be packed into the vascular cavity to form the occlusion in the vascular cavity and coupled to the distal portion of the core wire. As a result, endovascular occlusion of the vascular cavity can be performed.

In one embodiment, the elongate tip portion is a long and substantially pliable segment adapted to be multiply folded upon itself to substantially pack said vascular cavity.

In another embodiment, the elongate tip portion is a segment adapted to be disposed in said vascular cavity and having a plurality of filaments extending therefrom to substantially pack said vascular cavity when disposed therein.

In still another embodiment, the microcatheter has a pair of radioopaque markers disposed thereon and the core wire has a radioopaque marker disposed thereon. The marker on the core wire is positioned in the proximity of one of the pair of markers on the microcatheter when the core wire is fully deployed. The other marker on the core wire marks the position of the catheter tip.

The invention is still further characterized as a microcatheter system for use in formation of an occlusion within a vascular cavity comprising a microcatheter having a distal end adapted for disposition in the proximity of the vascular cavity. The distal end has an electrode disposed thereon. A conductive guidewire is disposed in the microcatheter and longitudinally displaceable therein. The guidewire comprises a core wire, and an elongate tip portion extending the core wire for a predetermined lineal extent. The tip portion is adapted to be packed into the vascular cavity to form the occlusion in the vascular cavity. The tip portion is coupled to the distal portion of the core wire. The occlusion is formed by means of applying a current between the tip portion and the electrode on the microcatheter when the tip portion is disposed into the vascular cavity. As a result, endovascular occlusion of the vascular cavity can be performed.

More generally speaking, the invention is a method for forming an occlusion within a vascular cavity having blood disposed therein comprising the steps of disposing a body into the cavity to substantially impede movement of blood in the cavity. The body is employed in the cavity to form the occlusion within the vascular cavity. As a result, the vascular cavity is occluded by the body.

The step of disposing the body in the vascular cavity comprises the step of packing the body to substantially obstruct the cavity.

In one embodiment the step of packing the cavity with the body comprises the step of obstructing the cavity with a detachable elongate wire tip multiply folded upon itself in the cavity.

The step of disposing the body into the vascular cavity comprises disposing in the vascular cavity means for slowing blood movement in the cavity to initiate formation of the occlusion in the cavity.

In another embodiment the step of packing the cavity with the body comprises the step of obstructing the cavity with a body having a compound filamentary shape.

The step of employing the body in the vascular cavity to form the occlusion comprises the step of applying an electrical current to the body or mechanically forming the occlusion in the body or both simultaneously.

The invention is also wire for use in formation of an occlusion within a vascular cavity used in combination with a microcatheter. The invention comprises a core wire and a detachable elongate tip portion extending the core wire for a predetermined lineal extent. The core wire is adapted to being packed into the vascular cavity to form the occlusion in the vascular cavity and is coupled to the distal portion of the core wire. The tip portion includes a first segment for disposition into the cavity and a second segment for coupling the first portion to the core wire. The second segment is adapted to be electrolysized upon application of current. An insulating coating is disposed on the first segment. The second segment is left exposed to permit selective electrolysis thereof. As a result, endovascular occlusion of the vascular cavity can be performed.

The invention can better be visualized by now turning to the following drawings wherein like elements are referenced by like numerals.

BRIEF DESCRIPTION OF THE DRAWINGS

FIGS. 1 and 1A are enlarged partially cross-sectioned side views of a first embodiment of the distal end of the guidewire and tip of the invention.

FIGS. 2 and 2A are enlarged longitudinal cross sections of a second embodiment of the guidewire and tip of the invention.

Figure 3:
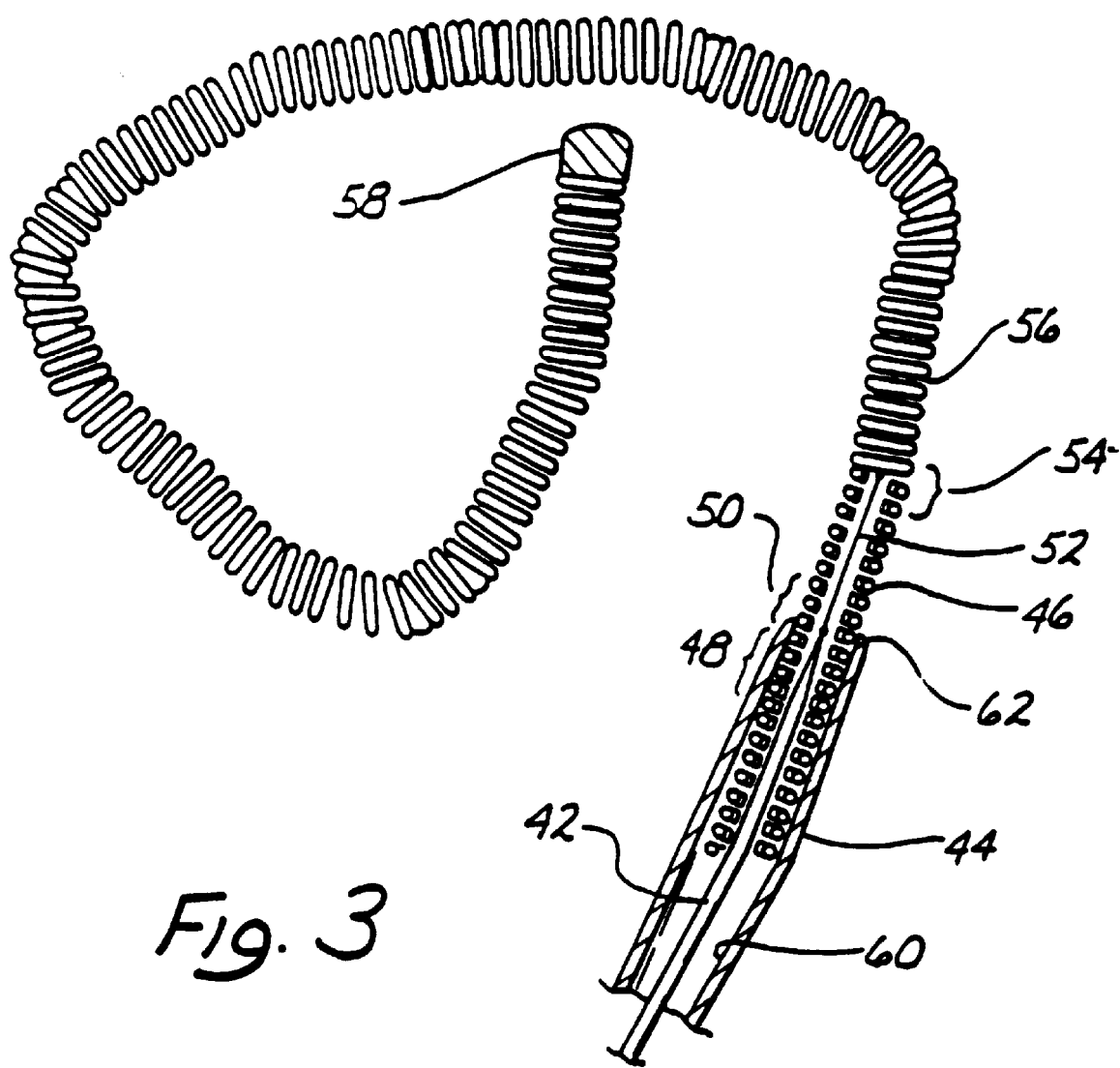
FIG. 3 is an enlarged side view of a third embodiment of the invention with a microcatheter portion cut away in a longitudinal cross-sectional view.

The invention and its various embodiments are best understood by now turning to the following detailed description.

DETAILED DESCRIPTION OF THE PREFERRED EMBODIMENTS

An artery, vein, aneurysm, vascular malformation or arterial fistula is occluded through endovascular occlusion by the endovascular insertion of a platinum tip into the vascular cavity. The vascular cavity is packed with the tip to obstruct blood flow or access of blood in the cavity such that the blood clots in the cavity and an occlusion if formed. The tip may be elongate and flexible so that it packs the cavity by being folded upon itself a multiple number of times, or may pack the cavity by virtue of a filamentary or fuzzy structure of the tip. The tip is then separated from the wire mechanically or by electrolytic separation of the tip from the wire. The wire and the microcatheter are thereafter removed leaving the tip embedded in the thrombus formed within the vascular cavity. Movement of wire in the microcatheter is more easily tracked by providing a radioopaque proximal marker on the microcatheter and a corresponding indicator marker on the wire. Electrothrombosis is facilitate by placing the ground electrode on the distal end of the microcatheter and flowing current between the microcatheter electrode and the tip.

When the tip is separated from the wire by electrolytic separation of the tip from the wire, a portion of the wire connected between the tip and the body of the wire is comprised of stainless steel and exposed to the bloodstream so that upon continued application of a positive current to the exposed portion, the exposed portion is corroded away at least at one location and the tip is separated from the body of the wire.

FIG. 1 is an enlarged side view of a first embodiment of the distal end of the wire and tip shown in partial cross-sectional view. A conventional Teflon laminated or similarly insulated stainless steel wire 10 is disposed within a protective microcatheter (not shown). Stainless steel wire 10 is approximately 0.010–0.020 inch (0.254–0.508 mm) in diameter. In the illustrated embodiment, wire 10 is tapered at its distal end to form a conical section 12 which joins a section 14 of reduced diameter which extends longitudinally along a length 16 of wire 10. Section 16 then narrows gradually down to a thin threadlike portion 18 beginning at a first bonding location 20 and ending at a second bonding location 22.

The stainless steel wire 10, comprised of that portion disposed within the microcatheter body, tapered section 12, reduced diameter section 16 and threadlike section 18, is collectively referred to as a core wire which typically is 50–300 cm. in length.

In the illustrated embodiment the portion of the core wire extending from tapered section 12 to second bonding location 22 is collectively referred to as the grinding length and may typically be between 20 and 50 cm. in length.

Reduced diameter portion 14 and at least part of sections 12 and first bonding location 20 may be covered with an insulating Teflon laminate 24 which encapsulates the underlying portion of wire 10 to prevent contact with the blood.

A stainless steel coil 26 is soldered to the proximate end of threadlike portion 18 of wire 10 at first bonding location 20. Stainless steel coil 26 is typically 3 to 10 cm. in length and like wire 10 has a diameter typically between 0.010 to 0.020 inch (0.254–0.508 mm).

The distal end of stainless steel coil 26 is soldered to the distal end of threadlike portion 18 of wire 10 and to the proximal end of a platinum secondary coil 28 at second bonding location 22. Secondary coil 28 itself forms a spiral or helix typically between 2 to 10 mm. in diameter. The helical envelope formed by secondary coil 28 may be cylindrical or conical. Like wire 10 and stainless steel coil 26, secondary coil 28 is between approximately 0.010 and 0.020 inch (0.254–0.508 mm) in diameter. The diameter of the wire itself forming stainless steel coil 26 and coil 28 is approximately between 0.001–0.005 inch.

The distal end of secondary coil 28 is provided with a platinum soldered tip to form a rounded and smooth termination to avoid puncturing the aneurysm or tearing tissue.

Although prebiased to form a cylindrical or conical envelope, secondary coil 28 is extremely soft and its overall shape is easily deformed. When inserted within the microcatheter (not shown), secondary coil 28 is easily straightened to lie axially within the microcatheter. Once disposed out of the tip of the microcatheter, secondary coil 28 forms the shape shown in FIG. 1 and may similarly be loosely deformed to the interior shape of the aneurysm.

As will be described below in greater detail in connection with the third embodiment of FIG. 3, after placement of secondary coil 28 within the interior of the aneurysm, a direct current is applied to wire 10 from a voltage source exterior to the body. The positive charge on secondary coil 28 within the cavity of the aneurysm causes a thrombus to form within the aneurysm by electrothrombosis. Detachment of the tip occurs either: (1) by continued application of current for a predetermined time when the portion 18 is exposed to blood; or (2) by movement of the wire to expose portion 18 to blood followed by continued current application for a predetermined time. Ultimately, both threadlike portion and stainless steel coil 26 will be completely disintegrated at least at one point, thereby allowing wire 10 to be withdrawn from the vascular space while leaving secondary coil 28 embedded within the thrombus formed within the aneurysm.

FIG. 2 illustrates in enlarged partially cross-sectional view a second embodiment of the invention Stainless steel core 32 terminates in a conical distal portion 34. Stainless steel coil 36, shown in cross-sectional view, is soldered to distal portion 34 of wire 32 at bonding location 38. The opposing end of the stainless steel coil 36 is provided with a soldered, rounded platinum tip 40. In the illustrated embodiment, stainless steel core wire 32 is approximately 0.010 inch in diameter with the length of stainless steel coil 36 being approximately 8 cm. with the longitudinal length of platinum tip 40 being between 3 and 10 mm. The total length of wire 32 from tip 40 to the proximate end is approximately 150 cm.

The embodiment of FIG. 2 is utilized in exactly the same manner as described above in connection with FIG. 1 to form a thrombic mass within an aneurysm or other vascular cavity. The embodiment of FIG. 2 is distinguished from that shown in FIG. 1 by the absence of the extension of stainless core 32 through coil 36 to tip 40. In the case of the embodiment of FIG. 2 no inner core or reinforcement is provided within stainless steel coil 36. Threadlike portion 18 is provided in the embodiment of FIG. 1 to allow increased tensile strength of the wire. However, a degree of flexibility of the wire is sacrificed by the inclusion even of threadlike tip 18, so that the embodiment of FIG. 2 provides a more flexible tip, at least for that portion of the micro-guidewire constituting the stainless steel coil 36.

It is expressly understood that the helical secondary coil tip of the embodiment of FIG. 1 could similarly be attached to stainless steel coil 36 of the embodiment of FIG. 2 without departing from the spirit and scope of the invention.

Thinned and threadlike portion guidewires disposed concentrically within coiled portions are well known and are shown in Antoshkiw, "*Disposable Guidewire*", U.S. Pat. No. 3,789,841 (1974); Sepetka et al., "*Guidewire Device*", U.S. Pat. No. 4,832,047 (1989); Engelson, "*Catheter Guidewire*", U.S. Pat. No. 4,884,579 (1989); Samson et al., "*Guidewire for Catheters*", U.S. Pat. No. 4,538,622 (1985); and Samson et al., "*Catheter Guidewire with Short Spring Tip and Method of Using the Same*", U.S. Pat. No. 4,554,929 (1985).

Turn now to the third embodiment of the invention as shown in FIG. 3. FIG. 3 shows an enlarged side view of a wire, generally denoted by reference numeral 42, disposed within a microcatheter 44 shown in cross-sectional view. Like the embodiment of FIG. 1, a stainless steel coil 46 is soldered to a conical portion 48 of wire 22 at a first bonding location 50. A thin threadlike extension 52 is then longitudinally disposed within stainless steel coil 46 to a second bonding location 54 where stainless steel wire 46 and threadlike portion 52 are soldered to a soft platinum coil 56. Platinum coil 56 is not prebiased, nor does it contain any internal reinforcement, but is a free and open coil similar in that respect to stainless steel coil 36 of the embodiment of FIG. 2.

However, platinum coil 56 is particularly distinguished by its length of approximately 1 to 50 cm. and by its flexibility.

The platinum or platinum alloy used is particularly pliable and the diameter of the wire used to form platinum coil 56 is approximately 0.001–0.005 inch in diameter. The distal end of platinum coil 56 is provided with a smooth and rounded platinum tip 58 similar in that respect to tips 30 and 40 of FIGS. 1 and 2, respectively.

When coil 56 is disposed within microcatheter 44, it lies along the longitudinal lumen 60 defined by microcatheter 44. The distal end 62 of microcatheter 60 is then placed into the neck of the aneurysm and the wire 42 is advanced, thereby feeding tip 58 in platinum coil 56 into aneurysm 64 until bonding location 50 resides in the neck of the aneurysm as best depicted in the diagrammatic cross-sectional view of FIG. 4.

Figure 4:
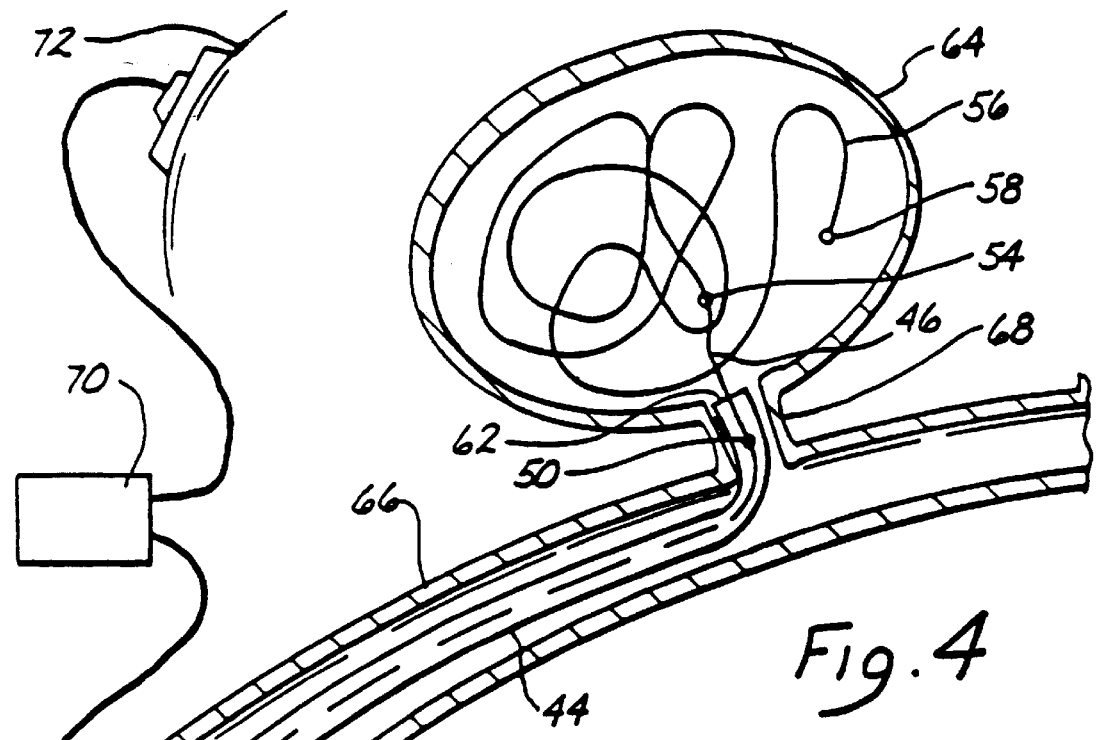
FIG. 4 is a simplified depiction of the wire of FIG. 3 shown disposed within a simple cranial aneurysm.

FIG. 4 illustrates the insertion of the embodiment of FIG. 3 within a vessel 66 with distal tip of microcatheter 44 positioned near neck 68 of aneurysm 64. Coil 56 is fed into aneurysm 64 until at least a portion of stainless steel coil 46 is exposed beyond the distal tip 62 of microcatheter 44. A positive electric current of approximately 0.01 to 2 milliamps at 0.1–6 volts is applied to wire 42 to form the thrombus. Typically a thrombus will form within three to five minutes. The negative pole 72 of voltage source 70 is typically placed over and in contact with the skin.

After the thrombus has been formed and the aneurysm completely occluded, tip 58 and coil 56 are detached from wire 42 by electrolytic disintegration of at least one portion of stainless steel coil 46. In the illustrated embodiment this is accomplished by continued application of current until the total time of current application is almost approximately four minutes.

At least one portion of stainless steel coil 46 will be completely dissolved through by electrolytic action within 3 to 10 minutes, usually about 4 minutes. After separation by electrolytic disintegration, wire 42, microcatheter 44 and the remaining portion of coil 46 still attached to wire 42 are removed from vessel 66, leaving aneurysm 64 completely occluded as diagrammatically depicted in FIG. 5 by thrombus 74. It will be appreciated that the time of disintegration may be varied by altering the dimensions of the portions of the wire and/or the current.

The process is practiced under fluoroscopic control with local anesthesia at the groin. A transfemoral microcatheter is utilized to treat the cerebral aneurysm. The platinum is not affected by electrolysis and the remaining portions of the microcatheter are insulated either by a Teflon lamination directly on wire 42 and/or by microcatheter 44. Only the exposed portion of the wire 46 is affected by the electrolysis.

It has further been discovered that thrombus 74 continues to form even after detachment from wire 42. It is believed that a positive charge is retained on or near coil 56 which therefore continues to attract platelets, white blood cells, red blood cells and fibrinogen within aneurysm 64.

Figure 6:
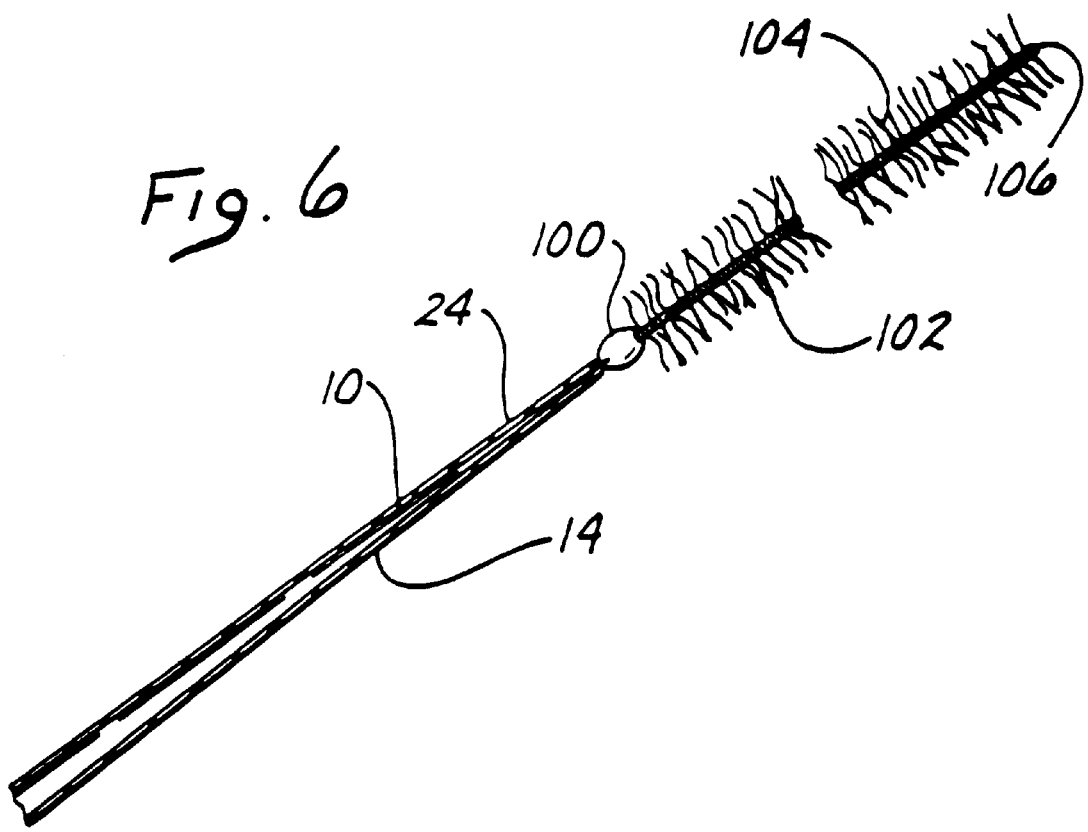
FIG. 6 is a plan view of another embodiment of the guidewire and tip portion wherein the type is provided with a plurality of polyester filamentary hairs.

Although the foregoing embodiment has been described as forming an occlusion within a blood-filled vascular cavity by means of electrothrombosis, the above disclosure must be read to expressly include formation of the occlusion by mechanical mechanisms without resort to the application of electrical current. A mechanical mechanism which can be safely disposed into the vascular cavity to impede, slow or otherwise initiate clotting of the blood or formation of the occlusion is within the scope of the invention. The insertion within the vascular cavity and maintenance therein of an object with an appropriate blood-clotting characteristics can and does in many cases cause the formation of an occlusion by itself. Depicted in FIG. 6 is an embodiment of the invention wherein such mechanical thrombosis can be achieved. Wire 10 has a tapering end portion 14 covered with a Teflon laminate 24 similar to that described in connection with the embodiment of FIG. 1. Wire 10 is attached by means of a mechanical coupling 100 to a platinum coil 102 which has a plurality of filaments or fine hairs 104 extending therefrom In the illustrated embodiment, hairs 104 have a length as may be determined from the size of the vascular cavity in which coil 102 is to be used. For example, in a small vessel hair lengths of up to 1 mm are contemplated. An example of polyester filaments or hairs attached to a coil which was not used in electrothrombosis may be seen in the copending application entitled Vasoocclusion Coil with Attached Fiberous Elements, filed Oct. 2, 1991, Ser. No. 07/771,013.

Coil 102 has sufficient length and flexibility that it can be inserted or coiled loosely into the vascular cavity. The length of coil 102 need not be so long that the coil itself is capable of being multiply folded on itself and fill or substantially fill the vascular cavity. Hairs 104 extending from coil 102 serve to substantially pack, fill or at least impede blood flow or access in the vascular cavity. Hairs 104, which are generally inclined backwardly away from extreme tip 106 when delivered, are thus easily able to slide forward with little friction through restrictions in the vessels and aneurysm. Additionally, hairs 104 do not have sufficient length, strength or sharpness to provide any substantial risk or potential for a puncture of the thin vascular wall. The plurality of hairs 104, when coiled within the vascular cavity, provide an extremely large surface for attachment of blood constituents to encourage and enhance the formation of a mechanical occlusion within the vascular opening.

In the preferred embodiment, coil 102 is mechanically coupled to thin tapered portion 104 of wire 10 by means of a small drop of polyester 100. Polyester may be substituted for the gold solder of the previously described embodiments in order to reduce concern or risk of toxic reactions in the body.

Tip portion 104 may also be mechanically separated from wire 10 by means other than electrolysis. One method is make the connection between tip 104 and wire 10 by means of a spring loaded mechanical clasp (not shown). The clasps are retained on tip 104 as long as the clasps remain inside of the catheter, but spring open and release tip 104 when extended from the catheter. The catheter and clasps may then be removed from the insertion site. This type of mechanical connection is described in the copending application entitled, "Detachable Pusher-Vasoocclusive Coil Assembly with Interlocking Coupling", filed Dec. 12, 1991 with Ser. No. 07/806,979 which is incorporated herein by reference and assigned to Target Therapeutics Inc. An alternative nonresilient mechanical ball and clasp capturing mechanism is described in the copending application entitled "Detachable Pusher-Vasoocclusive Coil Assembly with Interlocking Ball and Keyway Coupling", filed Dec. 12, 1991 with Ser. No. 07/806,912 which is also incorporated herein by reference and assigned to Target Therapeutics Inc.

In another embodiment wire 10 and tip portion 104 screw into each other and can be unscrewed from each other by rotation of the catheter or wire with respect to tip 104. An extendable sheath (not shown) in the microcatheter is advanced to seize tip 104 to prevent its rotation with wire 10 during the unscrewing process. This type of mechanical connection is described in the copending application entitled "Detachable Pusher-Vasoocclusive Coil Assembly with Threaded Coupling", filed Dec. 12, 1991 with Ser. No. 07/806,898 which is incorporated herein by reference and assigned to Target Therapeutics Inc.

In any case the specific means disclosed here of mechanically detaching tip 104 from wire 10 forms no part of the present invention apart from its combination as a whole with other elements of the invention. Specific disclosure of the mechanical means of detachment have been set forth only for the purposes of providing an enabling disclosure of the best mode presently known for practicing the claimed invention.

Even where the occlusion is not formed by electrothrombosis, separation of tip 104 may be effected by electrolysis. In such situations, the electrolysing current may be concentrated on the sacrificial stainless steel portion of tip 104 by disposition of an insulative coating on the remaining platinum portion. For example, tip 104 may be provided with a polyethylene coating save at least a portion of the stainless steel length. This has the effect of decreasing the time required to electrolytically sufficiently disintegrate the steel portion to allow detachment of the platinum tip, which is an advantageous feature in those cases where a large aneurysm must be treated and a multiple number of coils must be deployed within the aneurysm.

Figure 7:
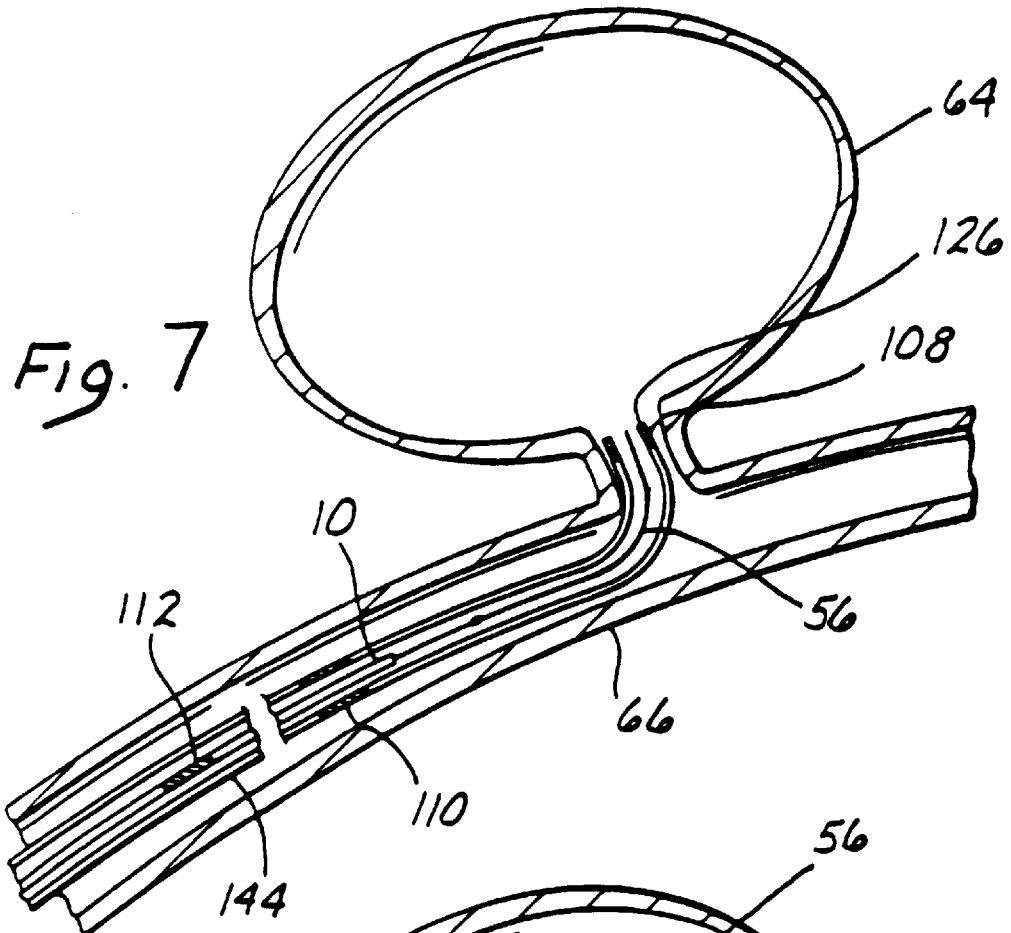
FIGS. 7 and 8 are a diagrammatic depictions of the use of the invention wherein position markers have been provided on the catheter and wire to assist in proper fluoroscopic manipulation.
Figure 8:
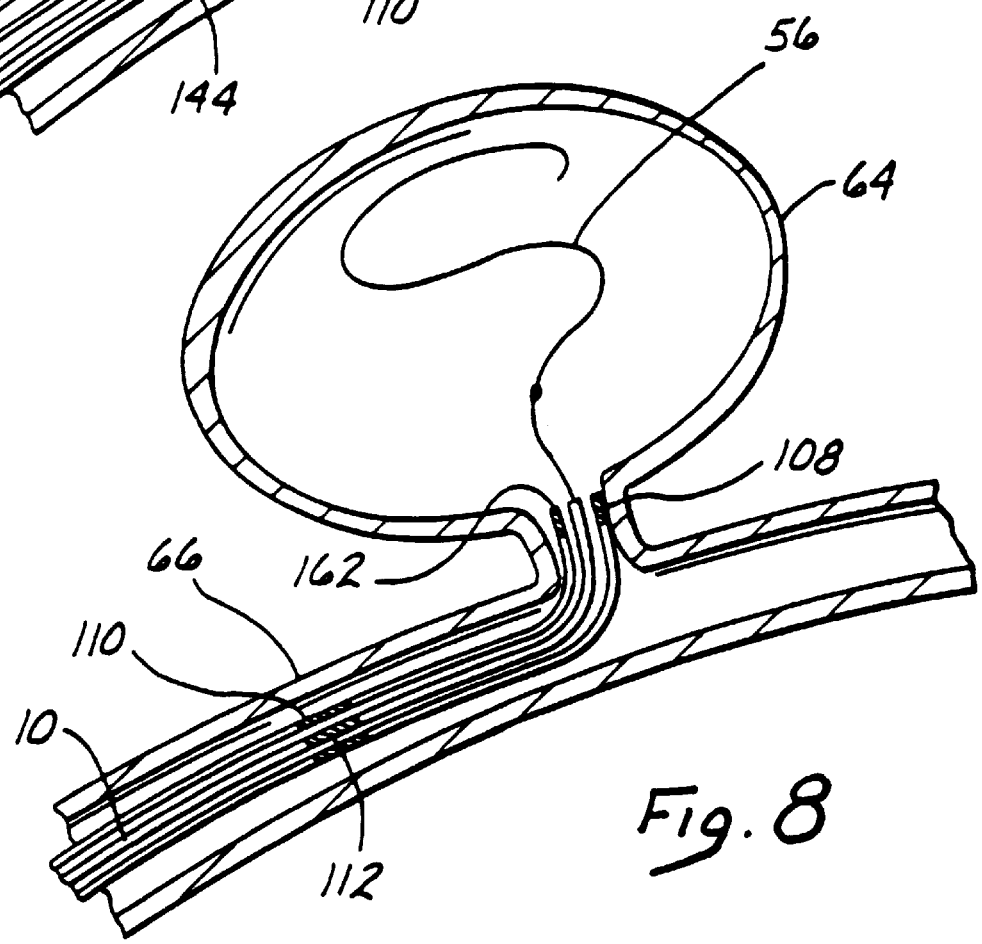

Notwithstanding the fact that wire 10 and platinum coil 102 in the embodiment FIG. 6 or wire 10 and platinum coil 28, 36 and 56 in the embodiments of FIGS. 1–5 are radiopaque, there is still some difficulty when manipulating the device under fluoroscopy to be able to determine the exact position or movement of the probe relative to the aneurysm. This is particularly true when a large number of coils are deployed and one coil then radiographically hides another. FIG. 7 illustrates an improvement of, for example, the embodiment of FIGS. 4 and 5. Microcatheter 144 is positioned so that its distal end 162 within vessel 66 is positioned at the opening aneurysm 64. Microcatheter 144 is provided with radiopaque marker 108 at distal tip 162, a tip marker. Moving toward the proximal end of microcatheter 144 is a second radiopaque marker 110, a proximal marker. Radiopaque markers 108 and 110 are, for example, in the form of radiopaque rings made of platinum, approximately 1–3 mm in longitudinal length along the axis of microcatheter 144. Rings 110 and 108 are typically separated by about 3 cm on microcatheter 144. Similarly, wire 10 has a radiopaque marker 112 defined on it such that marker 112 on wire 10 is approximately with aligned with marker 110 on microcatheter 14 when coil 56 is fully deployed into aneurysm 64. Typically, full deployment will place the solder or connection point 54 of the order of 2–3 mm past opening 68 of aneurysm 64. Distal marker 108 on microcatheter 144 is used to facilitate the location of the microcatheter tip, which can often be obscured by the coils which have been previously deployed. The coils are a varying lengths depending on the application or size of the aneurysm or vascular cavity being treated. Coil lengths of 4–40 cm are common. Therefore, even though the thinness of coil 56 may make it difficult to see under standard fluoroscopy and even though the fineness of wire 10 may similarly be obscured or partly obscured, radiopaque markers 108, 110 and 112 are clearly visible. Manipulation of wire 10 to proximal marker 110 can then easily be observed under conventional fluoroscopy even when there are some loss of resolution or fluoroscopic visual obstruction of the coil.

Figure 5:
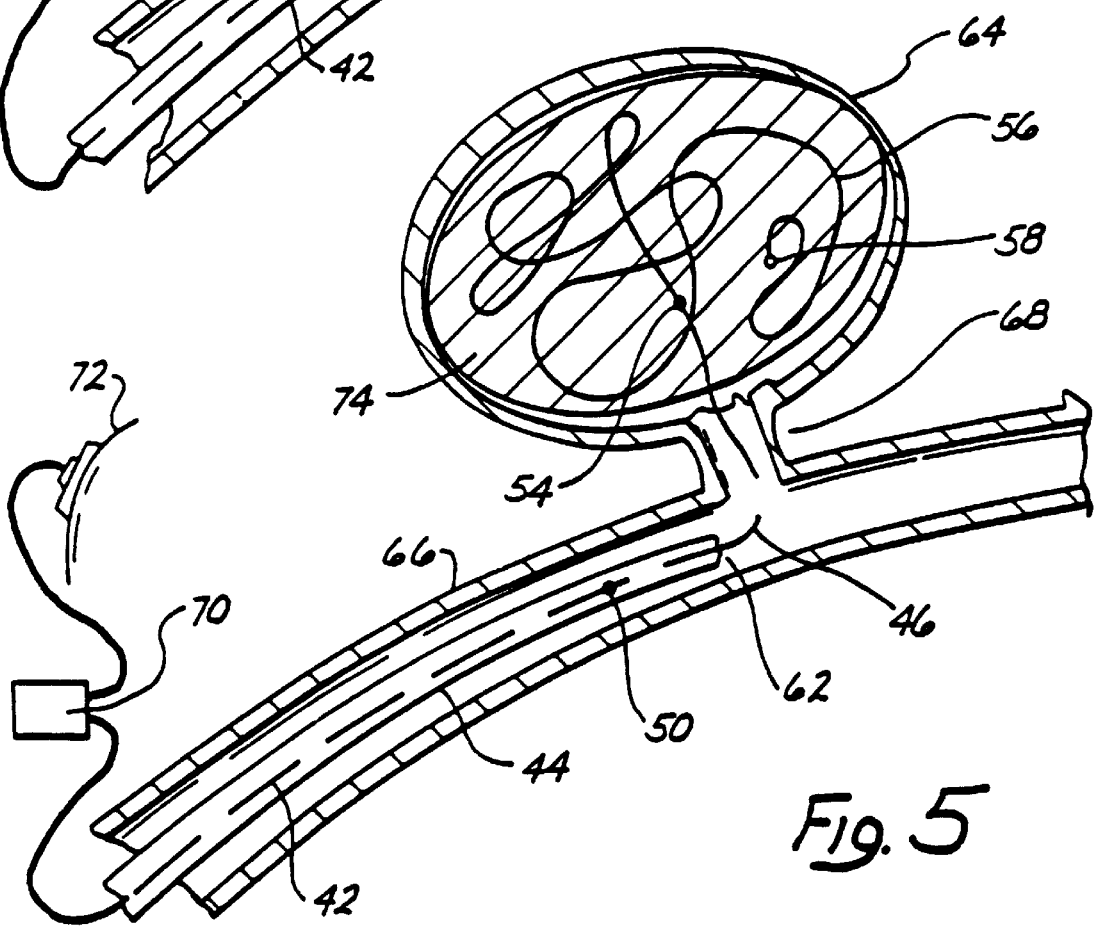
FIG. 5 is a depiction of the wire of FIG. 4 shown after electrolytic detachment of the tip.
Figure 9:
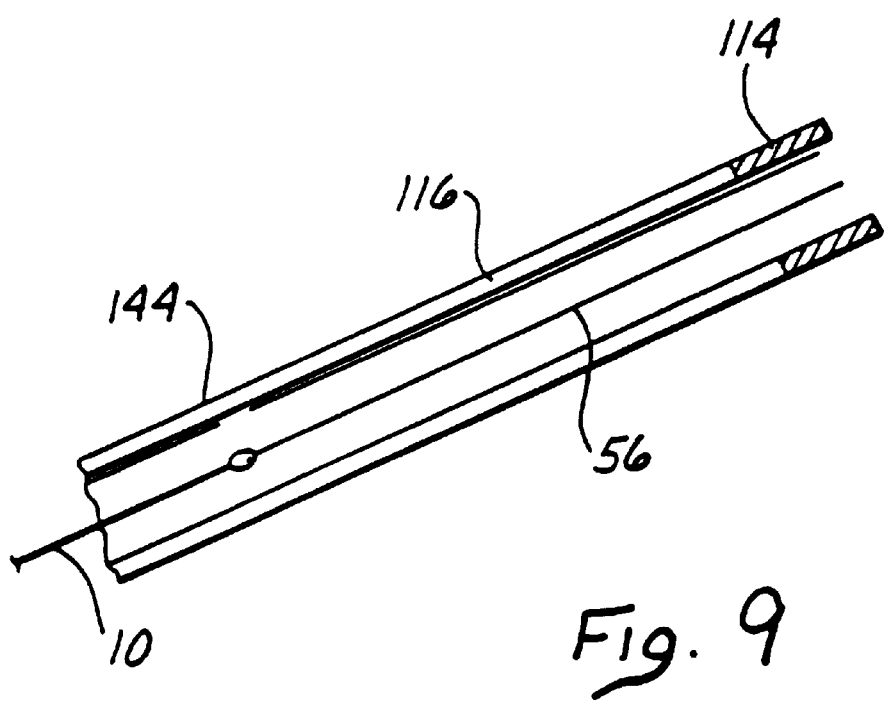
FIG. 9 is a simplified cross-sectional view of the catheter and wire showing a ground electrode disposed on the distal tip of the catheter.

Further, in the previous embodiments, such as that shown in FIGS. 4 and 5, when electrothrombosis is used to form the occlusion within vascular aneurysm 64, coil 56 is used as the electrical anode while the cathode is a large skin electrode 72 typically conductively applied to the groin or scalp. FIG. 9 illustrates an alternative embodiment wherein microcatheter 144 is supplied with an end electrode 114 coupled to an electrical conductor 116 disposed along the length of microcatheter 144. Wire 116 is ultimately led back to voltage source 70 so that ring electrode 114 is used as the cathode during electrothrombosis instead of an exterior skin electrode 72. With the embodiment of FIG. 9, the electrical currents and electrical current paths which are set up during the electrothrombosis formation are local to the site of application which allows even smaller currents and voltages to be used to initiate electrothrombosis than in the situation when an exterior skin electrode must be utilized. The electrothrombosic current distributions are also better controlled and localized to the site of the thrombus formation. The possibility of stray thrombus formations occurring at unwanted sites or uncontrolled and possibly unwanted electrical current patterns being established elsewhere in the brain or body is therefore largely avoided.

Many alterations and modifications may be made by those having ordinary skill in the art without departing from the spirit and scope of the invention Therefore, it must be understood that the shape of the tip or distal platinum coil used in combination with the wire according to the invention may be provided with a variety of shapes and envelopes. In addition thereto, the composition of the micro-guidewire tip may be made of elements other than platinum including stainless steel beryllium, copper and various alloys of the same with or without platinum. Still further, the diameter of the wire, various of the wire described above and the stainless steel coil immediately proximal to the detachable tip may be provided with differing diameters or cross sections to vary the times and current magnitudes necessary in order to effectuate electrolytic detachment from the tip. Still further, the invention may include conventional electronics connected to the proximal end of the wire for determining the exact instant of detachment of the distal tip from the wire.

Therefore, the illustrated embodiment has been set forth only for the purposes of clarity and example and should not be taken as limiting the invention as defined by the following claims, which include all equivalent means whether now known or later devised.

We claim:

1. An apparatus for forming an occlusion within a body cavity comprising:

a wire adapted to be disposed near an opening into said body cavity;

a separable distal tip of said wire adapted for disposition into said body cavity to form said occlusion within said body cavity about said distal tip; and a selectively detachable coupling between said distal tip and said wire characterized by detachment of said distal tip from said wire without necessarily displacing either said distal tip or said wire during detachment to leave said distal tip within said body cavity with said occlusion being formed within said body cavity, whereby said body cavity is occluded by said distal tip, and an occlusion is formed by use of said tip without necessarily altering desired placement of said distal tip during detachment or applying any force by said distal tip to any surface within said body cavity by reason of said detachment.

2. The apparatus of claim 1 where said distal tip has a length and flexibility to allow said distal tip sufficiently to fill said body cavity to impede flow of a fluid in said body cavity when said distal tip is disposed in said body cavity.

3. The apparatus of claim 1 where said distal tip is a coil having a length between 1 and 50 cm.

4. The apparatus of claim 1 where said coupling detaches by electrolytic detachment of said distal tip from said wire.

5. The apparatus of claim 4 where said coupling electrolytically detaches said distal tip from said wire by electrolytically disintegrating at least one portion of a connecting segment extending between said wire and said distal tip.

6. The apparatus of claim 1 where said distal tip is a coil that is prebiased to form a helix.

7. The apparatus of claim 6 where said coil is a stainless steel coil segment.

8. The apparatus of claim 1 where said distal tip includes a thread or filament that provides increased tensile strength to said distal tip.

9. The apparatus of claim 8 wherein a fluid is present within said body cavity and further comprising a catheter in which said wire, distal tip and coupling are disposed, and where said coupling is not exposed to said fluid during a first predetermined time period by being disposed within said catheter to allow formation of said occlusion about said distal tip, and is exposed to said fluid during an additional predetermined time period to separate said distal tip from said wire by being disposed outside of said catheter.

10. The apparatus of claim 1 where said distal tip is detached from said wire by applying a positive direct current to said distal tip for a predetermined time period.

11. The apparatus of claim 1 wherein a fluid is present within said body cavity and wherein said wire is adapted to be disposed in a first configuration relative to said body cavity so that a disintegratable portion of said tip remains insulated from said fluid during application of a first electrical signal to said tip, and where said disintegratable portion of said tip is adapted to assume to a second configuration where said disintegratable portion is exposed to said fluid when a second electrical signal is applied to said disintegratable portion to electrolytically dissolve said disintegratable portion in said fluid.

12. An apparatus for use in formation of an occlusion within a body cavity comprising:
a wire having at least an electrolyzable distal portion; and
a separable elongate tip portion of said wire coupled to and extending from said wire, said separable elongate tip portion adapted to form said occlusion in said body cavity and being adapted for insertion within said body cavity, said separable elongate tip portion being resistant to electrolysis compared to said distal portion of said wire, said separable elongate tip portion being coupled to said wire by said electrolyzable distal portion,
whereby occlusion of said body cavity is achieved.

13. The apparatus of claim 12 wherein said distal portion of said wire is an exposed stainless steel segment.

14. The apparatus of claim 12 wherein said electrolyzable distal portion comprises a coil having a proximal and distal end and is connected at its proximal end to said wire and connected at its distal end to said elongate tip portion of said apparatus.

15. The apparatus of claim 12 wherein said separable elongate tip portion of said wire includes a stainless steel coil and wherein said wire is extended in a threadlike portion concentrically within said stainless steel coil from a proximal end of said stainless steel coil to where said stainless steel coil is connected to said elongate tip portion of said apparatus.

16. The apparatus of claim 12 wherein said separable elongate tip portion of said wire includes a coil and wherein said coil defines an interior space, said interior space being free and unreinforced.

17. The apparatus of claim 12 wherein said separable elongate tip portion is a long and substantially flexible segment and is comprised of a metal not as susceptible to electrolytic disintegration as said wire.

18. The apparatus of claim 17 wherein said long and flexible segment of said elongate tip portion has a length which substantially occupies said body cavity when inserted therein to substantially impede flow of fluid in said body cavity.

19. The apparatus of claim 12 wherein said separable elongate tip portion is comprised of platinum or platinum alloy.

20. The apparatus of claim 12 where said separable elongate tip portion is arranged and configured by composition and size to electrolytically detach in less than four minutes.

21. An apparatus for use in formation of an occlusion used in combination with a catheter comprising:
an electrolyzable core wire; and
a separable elongate tip portion extending said core wire for a predetermined lineal extent and coupled to a distal portion of said core wire, said separable elongate tip portion for insertion within a body cavity, said separable elongate tip portion not resistant to electrolytic disintegration in fluid as compared to said electrolyzable core wire, said separable elongate tip portion being separable from said core wire by electrolysis,
wherein said separable elongate tip portion is a long and substantially flexible segment and is comprised of a metal not as susceptible to electrolytic disintegration within fluid as said core wire, and
wherein said long and flexible segment is prebiased to form a helix when extended from said catheter,
whereby occlusion of said body cavity is achieved.

22. The apparatus of claim 21 wherein said helix has a conical envelope.

23. The apparatus of claim 21 wherein said helix has a cylindrical envelope.

24. The apparatus of claim 21 where said separable elongate tip portion is arranged and configured by composition and size to electrolytically detach in less than four minutes.

25. A method for forming an occlusion within a body cavity comprising the steps of:
disposing a wire near an opening into said body cavity;
disposing a separable distal tip of said wire into said body cavity to form said occlusion within said body cavity about said distal tip; and
detaching a coupling between said distal tip and said wire without necessarily displacing either said distal tip or said wire during detachment or applying a force by said distal tip to any surface within said body cavity to leave said distal tip within said body cavity with said occlusion being formed within said body cavity.

26. The method of claim 25 where said step of disposing said distal tip of said wire disposes said distal tip into said body cavity to occupy said cavity to a degree sufficient to impede flow of a fluid in said body cavity.

27. The method of claim 26 where said step of disposing said distal tip of said wire disposes a distal tip having a long and pliable length.

28. The method of claim 25 where said step of detaching said distal tip of said wire detaches said distal tip from said wire by electrolytic disintegration of a coupling between said distal tip and said wire.

29. The method of claim 28 where said step of detaching said distal tip of said wire electrolytically disintegrates a connecting segment coupling said wire to said distal tip to effect separation.

30. The method of claim 29 where said step of detaching said distal tip of said wire electrolytically disintegrates a coil segment.

31. The method of claim 30 where said step of detaching said distal tip of said wire electrolytically disintegrates a stainless steel coil segment.

32. The method of claim 25 further comprising the step of applying an electrical signal to said distal tip to form said occlusion by applying a positive direct current for a first predetermined time period.

33. The method of claim 32 where said step of applying an electrical signal to said distal tip to form said occlusion further applies a positive direct current to said distal tip for an additional predetermined time period separate from said first predetermined time period.

34. The method of claim 32 further comprising the step of shielding a coupling between said wire and distal tip from a fluid during said first predetermined time period by disposing said coupling in a catheter to allow formation of said occlusion about said distal tip, and then exposing said coupling to said fluid during an additional predetermined time period to separate said distal tip from said wire.

35. The method of claim 25 where detaching said distal tip of said wire separates said distal tip from said wire by applying a positive direct current to said distal tip for a predetermined time period.

36. The method of claim 25 where in said step of disposing said distal tip of said wire into said body cavity said wire is disposed in a first configuration relative to said body cavity so that a disintegratable portion of said tip remains insulated from a fluid in said body cavity during application of a first electrical signal to said tip, and is disposed in a second configuration where said disintegratable portion is exposed to said fluid when a second electrical signal is applied to said disintegratable portion to electrolytically dissolve said disintegratable portion in said fluid.

37. A method for forming an occlusion within a body cavity comprising the steps of:

disposing a core wire having at least an electrolyzable distal portion near an opening into said body cavity;

disposing a separable elongate tip portion coupled to and extending from said electrolyzable distal portion of said core wire through said opening into said body cavity, said separable elongate tip portion adapted to form said occlusion in said body cavity, said separable elongate tip portion being resistant to electrolysis compared to said distal portion of said core wire; and selectively detaching said separable elongate tip portion from said core wire by electrolysis, whereby occlusion of said body cavity is achieved.

38. The method of claim 37 where said step of disposing a core wire having at least an electrolyzable distal portion disposes a core wire having an exposed stainless steel segment.

39. The method of claim 38 wherein said step of disposing a core wire comprises disposing a coil having a proximal and distal end which is connected at its proximal end to said core wire and which is connected at its distal end to said elongate tip portion.

40. The method of claim 39 where said step of disposing a core wire disposes a threadlike portion concentric within said coil which extends from said proximal end of said coil to where said coil is connected to said elongate tip portion.

41. The method of claim 39 where said step of disposing a core wire disposes a coil which defines an interior space, said interior space being free and unreinforced.

42. The method of claim 37 where said step of disposing a separable elongate tip portion disposes a long and substantially flexible segment comprised of a metal not as susceptible to electrolytic disintegration as said core wire.

43. The method of claim 42 where said step of disposing a separable elongate tip portion disposes an elongate tip portion having a length sufficient to substantially impede flow of fluid in said body cavity when inserted therein.

44. The method of claim 37 where said step of disposing a separable elongate tip portion disposes a separable elongate tip portion comprised of platinum or platinum alloy.

45. A method of using a catheter to form an occlusion in a body cavity comprising:

disposing an electrolyzable core wire near the situs of said occlusion;

disposing a separable elongate tip portion extending from and coupled to said core wire at said situs of said occlusion, said separable elongate tip portion being more resistant to electrolytic disintegration in fluid than said electrolyzable core wire, and being a long substantially flexible segment prebiased to form a helix when extended from said catheter; and detaching said elongate tip portion from said core wire by electrolysis, whereby occlusion of said body cavity is achieved.

46. The method of claim 45 where said step of disposing said separable elongate tip portion disposes a helix with a cylindrical envelope.

47. The method of claim 45 where said step of disposing said separable elongate tip portion disposes said helix with a conical envelope.

* * * * *